(12) United States Patent
Clarke et al.

(10) Patent No.: US 8,604,084 B2
(45) Date of Patent: Dec. 10, 2013

(54) METHOD

(75) Inventors: Geoffrey Douglas Clarke, Parsippany, NJ (US); Timothy James Grattan, Surrey (GB); Ian Burnett, Nyon (CH)

(73) Assignee: GlaxoSmithKline, LLC, Philadelphia, PA (US)

( * ) Notice: Subject to any disclaimer, the term of this patent is extended or adjusted under 35 U.S.C. 154(b) by 180 days.

(21) Appl. No.: 13/055,477

(22) PCT Filed: Jul. 29, 2009

(86) PCT No.: PCT/US2009/052039
§ 371 (c)(1),
(2), (4) Date: Feb. 28, 2011

(87) PCT Pub. No.: WO2010/014661
PCT Pub. Date: Feb. 4, 2010

(65) Prior Publication Data
US 2011/0301243 A1 Dec. 8, 2011

(30) Foreign Application Priority Data
Jul. 30, 2008 (GB) .................................. 0813929.7

(51) Int. Cl.
*A61K 31/16* (2006.01)
(52) U.S. Cl.
USPC ........................................................ 514/630
(58) Field of Classification Search
USPC ........................................................ 514/630
See application file for complete search history.

(56) References Cited

U.S. PATENT DOCUMENTS

| 6,264,983 B1 * | 7/2001 | Upadhyay ..................... 424/464 |
| 2004/0126318 A1 | 7/2004 | Ephrepreis ..................... 424/9.1 |
| 2004/0170681 A1 | 9/2004 | Grattan ........................... 424/465 |
| 2007/0141144 A1 | 6/2007 | Roberts et al. ................. 424/464 |

FOREIGN PATENT DOCUMENTS

| GB | 2103087 A * | 2/1983 |
| WO | WO 02/100391 A1 | 12/2002 |
| WO | WO 2005/015344 A2 | 2/2005 |
| WO | WO 2006/049978 A1 | 5/2006 |
| WO | WO 2007/118063 A1 | 10/2007 |

OTHER PUBLICATIONS van Wyk et al. The proportional cumulative area under the curbe of paracetmaol used as an index of gastric emptying in diabetic patients with symptoms of gastroparesis. Clinical Experimental Pharamcology and Physiology (1995) 22, p. 637-640.*
Grattan, et al. *European Journal of Pharmaceutics and Biopharmaceutics*, 49(3): 225-229 (2000).
O'Mahoney, et al. *Drugs and Aging*, 19: 515-527 (2002).
Rostami-Hodjegan, et al. *Drug Development & Industrial Pharmacy*, 28(5): 533-543 (2002).

* cited by examiner

*Primary Examiner* — Jennifer M Kim
(74) *Attorney, Agent, or Firm* — Nora L. Stein; Theodore R. Furman

(57) ABSTRACT

The present invention is directed to a novel method for reducing intrapatient variability in pharmaceutically active agent which is suitably not absorbed in the stomach, such as paracetamol, containing formulations in patients having gastric dysmotility, or a method of improving analgesia in a diabetic patient, or improving absorption of an active agent is a patient with gastric dysmotility, which methods comprises administering orally to said patient in need thereof a pharmaceutical dosage form comprising a first active agent, calcium carbonate, at least one first binding agent, and at least one disintegrating agent as intragranular components in the form of a granulate, and as an extragranular component at least one hydrophilic colloid, an optionally a second binding agent, calcium carbonate, a super disintegrant, and a second active agent.

22 Claims, No Drawings

// METHOD

This application is a §371 national stage entry of International Application No. PCT/US2009/052039, filed 29 Jul. 2009 which claims the priority of GB 0813929.7, filed 30 Jul. 2008, which are incorporated herein in their entireties.

FIELD OF THE INVENTION

The present invention is directed to novel methods of use for paracetamol containing formulations which deliver rapid dissolution of the active agent followed by improved absorption in patients with delayed gastric emptying.

BACKGROUND OF THE INVENTION

The present invention is the use of a paracetamol formulation that has unexpectedly been shown to have improved pharmacokinetic profiles in patients having gastric dysmotility or gastroparesis. Historically, diabetes has been shown to reduce gastric motility (gastroparesis) by up to 50% in patients as compared to non-diabetic individuals.

Involvement of the autonomic nervous system in patient having diabetes mellitus includes gastric enteropathy characterized by gastrointestinal dysmotility. Bassotti, G., Recenti Prog Med. 82: 334-337 (1991). Long-standing diabetes mellitus may reduce gastric emptying in up to 50% of patients. O'Mahony et al., Drugs Aging, 19: 515-527 (2002). The impact of various age-related diseases on gastrointestinal motility in the elderly can also include those patients with depression which significantly prolongs whole-gut transit time; hypothyroidism, chronic renal failure, and idiopathic Parkinson's disease. Frequently drugs in the elderly can cause disordered gastrointestinal motility, such as anticholinergics, opioid analgesics and calcium antagonists.

The importance of dysmotility in patients, particularly the elderly, may result in serious clinical consequences where clinical response to a medication is delayed, such as in delayed levodopa absorption or with diuretics. As opioids and anticholinergics already have inhibitory effects on gastric emptying, this may delay the absorption of other drugs. Consequently, the need for consistent, low intrapatient variability on absorption of drugs, such as analgesics, in such a patient population is very much in need.

SUMMARY OF THE INVENTION

The present invention is directed to a novel method for reducing intrapatient variability in pharmaceutically active agent which is suitably not absorbed in the stomach, such as paracetamol containing formulations in patients having gastric dysmotility, and the present invention is directed to a method for improving analgesia in a diabetic patient, or for improving absorption of an active agent is a patient with gastric dysmotility, which methods all comprises administering orally to a patient in need thereof, a pharmaceutical dosage form comprising a first active agent, suitably paracetamol, calcium carbonate, at least one first binding agent, and at least one disintegrating agent as intragranular components in the form of a granulate, and as an extragranular component at least one hydrophilic colloid, an optionally a second binding agent, calcium carbonate, a super disintegrant, and a second active agent.

DETAILED DESCRIPTION OF THE INVENTION

The present invention is directed to a novel method of improving the variability of absorption of an active agent between patients who have gastric dysmotility. Gastric dysmotility is also known as gastric hypomotility. Gastric hypomotility, in otherwise normal patients, can be induced by a variety of environmental, pharmacological and physiological factors. Importantly, delayed gastric emptying can have a deleterious effect on the absorption of drugs such as paracetamol, which are absorbed primarily in the small intestine. This can result in delayed and inconsistent plasma levels of a medicine, and can cause discomfort when the particular medicine is a pain medicine such as paracetamol.

For purposes herein the active agent is suitably not one which is absorbed in the stomach. The present formulation is intended to introduce the active agent into the duodenum at an increased rate over an otherwise standard formulation of the active agent. Therefore, any active that is absorbed primarily after the pyloric sphincter (e.g., at the bottom of the stomach) rather than in the stomach itself is expected to show a more rapid, and a more consistent pharmacokinetic profile. As will be described herein in greater detail, the active agent, paracetamol has been chosen herein to describe the invention. Paracetamol in a standard dosage form has been shown to not contribute to the emptying rate of the drug from the stomach.

Paracetamol is an analgesic and antipyretic drug effective in relieving mild to moderate pain. The recommended therapeutic dose in the United Kingdom is 500-1000 milligrams (mg) every 4 to 6 hours (hr) up to a maximum of 4000 mg daily. The absolute oral bioavailability is about 80% and is independent of dose in the range of 5-20 mg/kg. Peak plasma levels are achieved between 0.5 and 3 hour post-dose depending on the formulation.

Paracetamol has a mean plasma half-life of 2.4 hours in adults with a range of 1.5-3.0 hours. It varies relatively little between individuals, and is not prolonged to a clinically significant extent at the extremes of age. It is not bound to plasma protein to any extent and the volume of distribution is about 0.9 litre/kilogram (1/kg) body weight.

Oral paracetamol is primarily absorbed from the upper small intestine and for standard solid dose tablet formulations the rate of absorption is limited by i) the process of tablet disintegration/dissolution and ii) by gastric emptying from the stomach into the upper small intestine.

Diabetes mellitus (type 2) is the most common cause of impaired gastrointestinal motility in the elderly. Gastric emptying can be abnormal in this population and therefore impact on the absorption profile of the active agent, such as paracetamol. The present invention has investigated the absorption profile of paracetamol from a standard dosage form and from a granulate dosage form of paracetamol and calcium carbonate, and has determined that the relative difference in absorption profiles observed in healthy volunteers is changed when using diabetic patients as a model of gastric dysmotility.

One embodiment of the present invention is directed to the use of a granulate composition of paracetamol as will be further described herein, that has now been shown to provide significantly greater absorption at 30 minutes, and to have statistically significant Cmax plasma levels at 30 minutes over standard paracetamol containing formulations in patients have gastric dysmotility. In one embodiment of the invention, those patients having gastric dysmotility are diabetic patients.

The present invention has also shown to provide significantly greater absorption at 60 minutes over standard paracetamol containing formulations in patient have gastric dysmotility.

While the present invention has also been shown to have a shorter time to maximal concentration (Tmax) as compared to standard paracetamol, however, the difference was not statistically significant. Overall the diabetic population shows slower absorption of paracetamol from both treatments when compared with results observed in healthy volunteers and this could be attributed in part to the gastric enteropathy that is known to occur in diabetes mellitus. Therefore, patients with type 2 diabetes are a suitable dysmotility model which can be used to evaluate the PK profile of paracetamol from two different formulations.

The paracetamol containing dosage form comprises paracetamol, calcium carbonate, at least one binding agent, and at least one disintegrating agent, as intragranular components in the form of a granulate, and as an extragranular component, a hydrophilic colloid, an optionally a binding agent, calcium carbonate, a super disintegrant, and/or additional paracetamol. A formula containing such excipients has been described in WO 2007/118063, filed 3rd Apr. 2007 whose disclosure is incorporated by reference herein in its entirety.

While not wishing to be limited to such a dosage form, it is also believed that the paracetamol containing dosage forms as described in Roberts et al., U.S. Pat. No. 2007/0141144, published Jun. 21, 2007 or an earlier but related WO publication, WO 2005/15344, published 8 Dec. 2005, whose disclosures are incorporated by reference herein, are also acceptable for use in the methods described herein.

A fast release composition according to this invention disintegrates and dissolves rapidly in the stomach so as to facilitate fast absorption of the active agent into the circulatory system. For purposes herein, "fast release" means wherein at least 60% of the active has dissolved from the composition at 180 seconds, as determined by the dissolution testing method described herein. In another embodiment, suitably at least 70%, of the active has dissolved. In another embodiment at least 80% has dissolved, and in yet another embodiment at least 90% of the active agent has dissolved from the composition at 180 seconds. A suitable dissolution testing method for this purpose utilizes the same conditions as disclosed in WO 02/100391, namely a USP paddle apparatus rotating at 30 rpm, employing 900 ml of 0.05M HCl at 37° C. as the dissolution medium. In this reference, the percentage of paracetamol dissolved was determined at fifteen minutes, rather than the 180 seconds as described in U.S. Pat. No. 2007/0141144. Also noted as suitable are the dissolution methods described at 5, 10, 15, 20, 25 and 30 minutes in Rostami-Hodjegan et al., Drug Development and Industrial Pharmacy, 28(5), pp 533-5439 (2002).

While paracetamol release rates have been determined for a number of commercially available paracetamol products and found to range from about 12% to about 32%, a fast release of the active is only part of the present invention. Not only must the active be released from its dosage form, the active must also be emptied from the stomach into the duodenum at a rate which is consistent from patient to patient, and in particular in patients with decreased gastric motility be emptied as near normal as possible.

Accordingly one aspect of the invention provides for a pharmaceutical composition comprising an active, calcium carbonate, at least one binding agent, and at least one disintegrating agent, as intragranular components in the form of a granulate.

The granulate may optionally be combined with one or more suitable extragranular components, and may be in the form of a "tablet" which may includes tablet of any shape, and includes caplets, which are tablets having a capsule shape. The formulation may be placed into capsules, or be available in unit dose sachets.

When in a unit dosage form, a composition according to the invention comprises a therapeutically effective amount of the active. In one embodiment the active is paracetamol, by which is meant an amount of paracetamol sufficient to achieve a therapeutic benefit. Suitably such an amount is in the range 250 mg to 1000 mg per unit dosage form (e.g. per tablet) and typically is either 325 mg or 500 mg.

While the active is present as an intragranular component, it is recognized that a limited amount of the same or a different active, may also be present extragranularly. Although it has not been prepared and tested, another embodiment of the invention includes a formulation wherein the active agent is solely dispersed in the formulation as extragranular component.

A pharmaceutical composition according to the invention comprises intragranular calcium carbonate. Suitably the calcium carbonate content in the granulate does not exceed 20.0% by weight of the composition, and for example in one embodiment is present in an amount of about 5.0% to about 20.0% by weight, suitably from about 5.0% to about 15.0% by weight of the composition. In an alternative embodiment the calcium carbonate content is from about 8.0% to about 15.0% by weight of the composition.

In one embodiment according to the invention the paracetamol content in the granulate is in the range 70.0 to 80.0% by weight of the composition and the calcium carbonate in the granulate is in the range 8.0% to 15.0% by weight of the composition. For example a 500 mg paracetamol composition may comprise 30 mg to 110 mg intragranular calcium carbonate, and a 325 mg paracetamol composition may comprise intragranular 20 mg to 72 mg calcium carbonate.

While calcium carbonate is present as an intragranular component, it is recognized that a limited amount of calcium carbonate e.g. up to about an additional 25.0% by weight of the intragranular calcium carbonate content of the composition, may also be present extragranularly. In one embodiment a composition according to the invention comprises, as an extragranular component, calcium carbonate in an amount ranging from about 0.1% to about 10.0% by weight of the intragranular calcium carbonate amount therein.

A composition according to the invention comprises intragranularly, a component that functions as a binder, such as one or more binding agents. Suitably the binding agent may comprise a first binding agent and a second binding agent. Suitable binding agents for use herein include conventional binding agents used in the art such as starches, polymers and cellulose derivatives or combinations thereof.

If the binding agent includes a starch, suitably it is of vegetable origin such as corn (or maize) starch, modified corn starch, wheat starch, modified wheat starch, potato starch, or pregelatinized starch e.g. available commercially as Starch 1500 G or Prejel; or a combination of two or more thereof.

Combinations of starch with other binding agents, such as those described herein, are also envisaged within the scope of the invention. In one embodiment, suitably the starch is pregelatinized starch, where it is the sole or a first binding agent. Pregelatinized starch is a starch that has been chemically and/or mechanically processed. Typically pregelatinized starch contains 5% of free amylase, 15% of free amylopectin, and 80% unmodified starch. Pregelatinized starch may be obtained from corn (or maize), potato or rice starch. It has been found that paracetamol dissolution rate is adversely affected in a composition comprising as intragranular components: paracetamol, calcium carbonate, maize starch, pregelatinized starch, Povidone K25, and potassium sorbate, wherein the weight ratio of pregelatinized starch to maize starch is about 2.3:1. Accordingly if the binding agent comprises a mixture of corn (or maize) starch and pregelatinized starch, then the weight ratio of pregelatinized starch to corn (or maize) starch is at least 3.0:1.0. In one embodiment of this invention, the weight ratio of pregelatinized starch to corn (or maize) starch is at least 5.0:1.0.

Suitably, when present in a composition of the invention, the starch is present in the granulate in an amount from about 1.0% to about 30.0% by weight of the composition, typically from about 5.0% to about 20.0% for example from about 8.0% to about 15.0% by weight of the composition.

If the binding agent includes a polymer, suitably it is polyvinyl pyrrolidone or povidone (PVP), polyvinyl alcohol (PVA), polyethylene oxide, polaxamer, polymethacrylate e.g. a carbomer, polyethylene glycol (PEG) such as PEG 3350 and calcium polycarbophil; or a combination of two or more thereof. Combinations of a polymer with other binding agents, such as those described herein, are also envisaged within the scope of the invention. When the polymer comprises PVP, it will suitably comprise a molecular weight of about 30,000 e.g. available commercially as PVP K25. Suitably, when present in a composition of the invention, the polymer is present in the granulate in an amount from about 1.0% to about 10.0% by weight of the composition, typically from about 1.5% to about 5.0% by weight of the composition.

In one embodiment, a polymer such as PVP is present as a second binding agent. In one embodiment a starch such as pregelatinized starch is present as a first binding agent, in an amount ranging from about 10.0% to about 15.0% by weight of the composition, and a polymer such as PVP is present as a second binding agent in an amount ranging from about 1.5% to about 5.0% by weight of the composition. Suitably such an embodiment is substantially free of corn (or maize) starch, for example comprising no more than an amount ranging from about 0.0% to about 1.0% of corn (or maize) starch.

If the binding agent includes a cellulosic derivative, suitably it includes at least one of hydroxypropyl cellulose (HPC) (low to medium viscosity versions thereof) e.g. as may be available commercially under the brand name Klucel® from the Aqualon division of Hercules Inc., Dow Chemical Company e.g. Klucel GF, Klucel JF, Klucel LF and Klucel EF; hydroxypropylmethyl cellulose (HPMC) (low to medium viscosity versions thereof) e.g. as may be available commercially under the brand name Methocel® from the Dow Chemical Company e.g. Methocel E15Premium, Methocel E3Premium LV, Methocel K100LV; microcrystalline cellulose (MCC), carboxymethylcellulose (MC), sodium carboxymethylethyl cellulose; or a combination of two or more thereof. Combinations of a cellulosic derivative with other binding agents noted above are also envisaged within the scope of the invention.

The term "low to medium" viscosity as used herein means a viscosity in the range of from about 15 to about 1000 mPa·s. It is recognized in the art that the determination of the viscosity of cellulosic derivatives is based upon standard techniques and grading in the art e.g. for HPMC, viscosity may be determined at 20° C. with a 2% solution using a Ubbelohde viscometer, or for HPC, viscosity may be determined at 25° C. with a 2-10% solution using a Brookfield LVF viscometer. Generally the cellulosic derivative is present in the granulate in an amount ranging from about 0.5% to about 5.0% by weight of the composition. It is recognized in the art that certain cellulosic derivatives, such as HPMC, will have varying roles in a formulation, depending upon the amount used. For example HPMC (low or medium viscosity) may function as a binding agent, a coating agent, or as a matrix forming agent. It has been found that when HPMC (low or medium viscosity) is used at about 10.0% by weight of the composition, the dissolution rate of paracetamol is slowed down, probably owing to the extended-release properties of HPMC.

According to the present invention, when used as a binding agent, the HPMC is present in an amount typically not more than 2.5% by weight of the composition, for example in an amount from about 1.0% to about 2.5% by weight of the composition.

The total amount of binding agent present intragranularly in a composition according to the invention is suitably in an amount ranging from about 1.0% to about 30.0% by weight of the composition, for example from about 2.0% to about 25.0% by weight of the composition, or alternatively from about 5.0% to about 20.0% by weight of the composition.

While a binding agent is present as an intragranular component, it is recognized that a modest amount of binding agent e.g. up to about an additional 5.0%-10.0% by weight of the intragranular binding agent content of the composition, may also be present extragranularly. In one embodiment a composition according to the invention comprises, as an extragranular component, a binding agent in an amount ranging from about 0.1% to about 10.0% by weight of the intragranular binding agent amount therein.

A composition according to the invention comprises, as an intragranular component, at least one component one that functions as a disintegrant, and may include at least two disintegrating agents. Suitable disintegrating agents include a non-super disintegrant, a super disintegrant or a combination of both. Suitable non-super disintegrants include conventional disintegrants such as starch (corn or maize), pregelatinized starch, e.g. Starch 1500 G, clays (Veegum or Bentonite), microcrystalline cellulose, cellulose or powdered cellulose. It is recognized in the art, that some excipients may perform more than one role in a given pharmaceutical formulation. For example certain excipients, e.g. starches including pregelatinized starch, and microcrystalline cellulose (hereinbefore identified as binding agents) function as both binders and disintegrants. Accordingly it will be understood that the same excipient may act as both a binding agent and a disintegrating agent. In such cases, inclusion of a disintegrating agent in addition to a binding agent is entirely optional. Equally, in such cases, inclusion of a binding agent in addition to a disintegrating agent is entirely optional.

One embodiment of the invention provides for as intragranular components, paracetamol and calcium carbonate, and at least one binding agent which is microcrystalline cellulose or starch, wherein the starch is corn (or maize) starch, modified corn starch, wheat starch, modified wheat starch, potato starch, pregelatinized starch or a combination of two or more starches thereof, with the proviso that if the binding agent comprises a mixture of corn (or maize) starch and pregelatinized starch then the weight ratio of pregelatinized starch to corn (or maize) starch is greater than from about 3.0 to 1.0; and optionally a disintegrating agent; and one or more pharmaceutically acceptable ingredients as extragranular components.

The compositions herein may include a non-super disintegrant which may be present intragranularly, extragranularly or both intragranularly and extragranularly. When a non-super disintegrant is either absent from the composition or is present only extragranularly, the disintegrating agent will suitably comprise a super disintegrant, present intragranularly.

Suitably a non-super disintegrant will be present intragranularly in an amount ranging from about 5.0% to about 30.0% by weight of the composition, suitably from about 5.0% to about 20.0% by weight of the composition. When present extragranularly, the non-super disintegrating agent, may also be present in an amount for example up to about an additional 5.0%-10.0% by weight of the intragranular non-super disintegrating agent content of the composition.

A super disintegrant, if used, may be present intragranularly, extragranularly or both intragranularly and extragranularly. It is recognized that when a super disintegrant is either absent from the composition or is present only extragranularly, the disintegrating agent will comprise a non-super disintegrant, present intragranularly. A super disintegrant may be used intragranularly or extragranularly, in an amount ranging from about 0.5% to about 5.0% by weight of the composition. The total amount of super disintegrant may be in an amount ranging from about 0.5% to about 10.0% by weight of the composition.

"Super disintegrants" represent a class of disintegrating agent which may generally be used in lower amounts in pharmaceutical preparations, as compared to conventional disintegrants. Examples of super disintegrants include sodium starch glycolate, the sodium salt of carboxymethyl starch, modified cellulose and cross-linked polyvinyl pyrrolidone. Sodium starch glycolate is available commercially under the trade names Explotab® (Edward Mendell Co.), Primojel® (Generichem Corp) and Tablo® (Blanver, Brazil). An example of modified cellulose includes croscarmellose, the sodium salt of carboxymethyl cellulose. Croscarmellose is available commercially under the trade names AcDiSol® (FMC Corp.), Nymcel ZSX® (Nyma, Netherlands), Primellose® (Avebe, Netherlands), Solutab® (Blanver, Brazil). An example of a cross-linked polyvinyl pyrrolidone includes crospovidone, and is commercially available under the trade names Kollidon CL® or Kollidon CL-M (Basf Corp.), and Polyplasdone XL® (ISP Corp). Suitably the disintegrating agent comprises cross-linked polyvinyl pyrrolidone.

A composition according to the invention may optionally contain further additional pharmaceutically acceptable extragranular components. For example a composition according to the invention may comprise a hydrophilic colloid such as alginic acid, carageenan, gellan, pectin and/or agar, as an extragranular component. Suitably the hydrophilic colloid is alginic acid. When present, a hydrophilic colloid is present in an amount ranging from about 1.0% to about 5.0% by weight of the composition.

In one aspect a composition according to the invention comprises alginic acid as an extragranular component.

Other pharmaceutically acceptable extragranular components include, but are not limited to, an antimicrobial agent e.g. potassium sorbate or a paraben i.e. one or more hydroxy benzoic acid esters e.g. methyl, ethyl. propyl or butyl, suitably singularly or as mixtures. In one embodiment of the invention a paraben is used.

In one embodiment the composition comprises paracetamol, calcium carbonate, pregelatinized starch, and povidone as intragranular components, and as extragranular components alginic acid and crospovidone, and optionally other extragranular components, preferably compressed into a tablet. Suitably, the alginic acid is present in an amount ranging from about 1.0% to about 5.0% by weight of the composition.

Additional pharmaceutically acceptable extragranular components include a dye; colorant; flavorant; compression aid; preservative; wetting agent; bulking agent; adhesive; sweetening agent; lubricant such as magnesium stearate, calcium stearate, sodium stearate, stearic acid or talc; and a flow aid or glidant such as colloidal silicon dioxide (Cab-O-Sil, Syloid™). Suitably, when present, a lubricant or flow aid are each used in an amount ranging from 0.1% to 5.0% by weight of the composition. It is recognized that additional pharmaceutically acceptable components may be present as intragranular components as well as extragranular components.

In addition to paracetamol, compositions of the invention may also contain other pharmaceutically active agents for example other analgesics such as codeine, hydrocodone, oxycodone, tramadol and propoxyphene; anti-inflammatory analgesics such as NSAIDs e.g. aspirin and ibuprofen; decongestants such as pseudoephedrine and phenylephrine; antitussives such as pholcodine and dextromethorphan; expectorants such as guaifenesin and bromhexine; diuretics such as pamabrom; non-sedating and sedating antihistamines such as diphenydramine, doxylamine and mepyramine; gastrointestinal agents such as metoclopramide; triptans such as sumatriptan; and muscle relaxants such as methocarbamol; and adjuvants, for example caffeine. As previously noted, pharmaceutically active agents and adjuvants may be present intragranularly, extragranularly or both intragranularly and extragranularly.

In another aspect there is provided a composition comprising caffeine intragranularly, extragranularly or both intragranularly and extragranularly. Suitably the caffeine is present extragranularly. In one embodiment the caffeine is in addition to an intragranular paracetamol containing formulation.

As used herein the term "pharmaceutically active agent" includes, but is not limited to, drugs, dietary supplements, vitamins, minerals, nutraceuticals, and veterinary agents. This term includes bioactive agents, active agents, therapeutic agents, or drug(s) as defined herein, and follows the guidelines from the European Union Guide to Good Manufacturing Practice. Such substances are intended to furnish pharmacological activity or other direct effect in the cure, mitigation, treatment, or prevention of disease or to affect the structure and function of the body. The pharmacological activity may be prophylactic, or for treatment of a disease state.

Drug substances include those intended for oral administration. A description of these classes of drugs and a listing of species within each class can be found in Martindale, The Extra Pharmacopoeia, Twenty-ninth Edition, The Pharmaceutical Press, London, 1989. The drug substances are commercially available and/or can be prepared by techniques known in the art.

The invention will now be described by reference to the following biological examples which are merely illustrative and are not to be construed as a limitation of the scope of the present invention.

EXAMPLE 1

Pharmacokinetic Profile in Gastric Dysmotility Patients

Long standing diabetes may have reduced gastric motility by up to 50%. Therefore, patients with type 2 diabetes were chosen as a dysmotility model to evaluate the PK profile of paracetamol from two different formulations. This study was a single centre, two way, open label, randomized, single dose, cross over PK study. Subjects received a single 1 gm oral dose of a formulation of the invention or standard paracetamol formulation, 2 hours after a standard meal, with randomly assigned patients having a 24 hour wash out between dosing. 21 patients completed the protocol, 18 males, and 3 females. Blood samples were taken 4 hours post-dose for pharmacokinetic analyses.

The primary study objective was to compare early exposure, as assessed by rate of absorption (area under the curve $[AUC]_{0\text{-}30\ mins}$). Other early exposure variables included time to maximum concentration ($T_{max}$), and inter-patient variability (coefficient of variation (CV)) in $AUC_{0-30\ mins}$, $AUC_{0-60\ mins}$ and plasma concentration ($C_{plasma}$) at 30 minutes.

Standard Panadol tablets are film coated tablets containing 500 mg paracetamol, and contain as excipients, pregelatinized starch, maize starch, talc, stearic acid, povidone, potassium sorbate, hypromellose, and glycerol triacetate.

The calcium carbonate/paracetamol formulation used herein contains 500 mg paracetamol and is similar to that described in Example 6 of WO 2007/118063.

Results:

| Parameter | Paracetamol/Calcium Carbonate Formula (n = 21) mean, median, CV % | Panadol Standard (n = 21) mean, median, CV % | Median difference | p-Value (Wilcoxon test) | p-Value (CV Square Rank test) |
|---|---|---|---|---|---|
| AUC0-30 min (ug/ml · h) | 0.45, 0.28, 153.1 | 0.14, 0.04, 215.8 | 0.18 | 0.0004 | 0.0522 |
| AUC0-60 min (ug/ml · h) | 2.10, 1.38, 102.8 | 0.84, 0.26, 174.9 | 1.02 | 0.0014 | 0.0801 |
| Cplasma at 30 mins (ug/ml) | 2.48, 1.52, 125.0 | 0.84, 0.19, 282.7 | 1.08 | 0.0002 | 0.0693 |
| Tmax (h) | 2.36, 2.50, 41.4 | 2.77, 2.75, 33.5 | −0.25 | 0.1448 | — |
| Cmax (ug/ml) | 8.99, 7.97, 34.9 | 9.49, 9.77, 28.9 | — | — | — |
| AUC0-tmin (ug/ml · h) | 21.01, 18.92, 35.1 | 18.5, 16.04, 7.9 | — | — | — |

$AUC_{0-30}$ min (primary objective) was statistically significantly greater for the Paracetamol/calcium carbonate containing formulation than for standard paracetamol (p=0.0004).

$AUC_{0-60}$ min and Cplasma at 30 minutes were statistically significantly greater (p=0.0014) and higher (p=0.0002), respectively, for Paracetamol/calcium carbonate containing formulation compared to standard paracetamol.

The time to maximum concentration (Tmax) was shorter for Paracetamol/calcium carbonate containing formulation compared to standard paracetamol but the difference was not statistically significant (p=0.1448).

There was a trend towards statistical significance for the comparison of CVs for $AUC_{0-30}$ min (p=0.0522), $AUC_{0-60}$ min (p=0.0801) and Cplasma at 30 minutes (p=0.0693) in favour of Paracetamol/calcium carbonate containing formulation.

The Paracetamol/calcium carbonate containing formulation was absorbed more rapidly than standard paracetamol tablets, and demonstrated a trend towards less inter-patient variability (based on the coefficient of variation) in this population of diabetic patients.

The planned sample size was less than desired, and may explain why there was a lack of statistical significance for the Tmax comparison obtained. Overall the tested population (diabetics) in this study showed slower absorption of paracetamol from both treatments when compared with results observed in healthy volunteers and this could be attributed in part to the gastric enteropathy that is known to occur in diabetes mellitus. However, the paracetamol/calcium carbonate containing formulation appears to maintain the advantages of fast and consistent absorption shown in previously healthy volunteers, even in those patients with diabetes mellitus.

EXAMPLE 2

Pharmacokinetic Parameter Study

It had previously been determined in a clinical study that the Paracetamol/calcium carbonate containing formulation (as described above) is emptied from the stomach more rapidly than a standard paracetamol (SP) tablet formulation. The study below compares the PK parameters of Paracetamol/calcium carbonate containing formulation and the standard paracetamol tablet, and to assesses their variability, since these can influence analgesic efficacy and response rates.

Methods:

A total of 76 healthy volunteers were recruited in an open-label, randomised, 8-way crossover study. Each formulation was administered in a replicate fashion, with a single 1 g dose taken 2 hours after a standard meal on 4 separate days. Blood samples were taken up to 10 hours after the initial dose and 4 hours after the replicate doses for pharmacokinetic (PK) analysis.

The primary objectives were: early exposure (rate of absorption, $AUC_{0-30\ mins}$, after both initial and replicate dosing), inter (between)-subject variation (inter-CV%, after initial dose) and intra-subject variation (intra-CV%, after replicate dosing). Secondary objectives included $AUC_{0-60\ mins}$, plasma concentration at 30 mins ($C_{pl\ 30\ mins}$) and percentage drug absorbed (PDA) at 30 and 60 minutes (measured by deconvolution analysis, variance measured for initial dose only).

Results:

$AUC_{0-30\ mins}$ for both the initial dose and after replicate dosing were very significantly higher for the Paracetamol/calcium carbonate containing formulation versus standard paracetamol formulation (initial dose: 0.98 versus 0.10 μg.h/ml [median difference 0.77, 95% CI 0.53-1.01, p<0.0001]; replicate dosing: 1.23 versus 0.15 μg.h/ml [median difference 0.99, 95% CI 0.81-1.19, p<0.0001]).

Inter-CV% for this parameter was significantly lower for the Paracetamol/calcium carbonate containing formulation versus standard paracetamol formulation (84.4% versus 192%, p<0.0001).

Similarly, there was a significant difference for intra-CV% for $AUC_{0-30\ mins}$ (60.6% versus 116%, p<0.0001). Similar reductions in inter-CV% and intra-CV% were observed for $AUC_{0-60\ mins}$ and $C_{pl\ 30\ mins}$ along with inter-CV% for $PDA_{30\ mins}$ and $PDA_{60\ mins}$.

Conclusions:

These data clearly show that paracetamol absorption with the Paracetamol/calcium carbonate containing formulation is significantly faster than absorption with standard paracetamol formulation tablets. Importantly, paracetamol absorption with the Paracetamol/calcium carbonate containing formulation also shows significantly less inter- and intra-subject variability. Taken together, these data have clear clinical implications in terms of a patient population obtaining rapid, and consistent, pain relief with this valuable first-line pain therapy and therefore avoiding potential side effect issues with second-line treatments such as the NSAIDs.

EXAMPLE 3

Disintegration and Gastric Emptying

Tablet disintegration and dissolution are key factors in in vivo speed of absorption and downstream pharmacokinetic parameters. Using the Paracetamol/calcium carbonate containing formulation an in vivo gamma scintigraphy investigation of tablet disintegration and gastric emptying (GE) was conducted.

Methods:

This single-dose, cross-over study involved 24 healthy volunteers. All participants ate a standard radio-labelled breakfast 2 hours (h) before taking the study medication (1 g paracetamol as either as Paracetamol/calcium carbonate containing formulation (described above) or a standard paracetamol tablet formulation described above (SP) [$^{111}$indium-DTPA-labelled tablet]).

The rate of disintegration was measured using gamma scintigraphy after defining the stomach area as the region of interest. Data were analysed using the WebLink® image analysis program. Onset and completion of tablet disintegration were determined by qualitative assessment of scintigraphic images. Tablet gastric emptying was determined by quantifying the amount of activity remaining in the stomach at a series of time points. Two parameters were used to assess GE: time to 50% emptying ($T_{50}$) and time to 90% emptying ($T_{90}$). Onset of GE was determined by qualitative assessment of scintigraphic images.

Results:

Both time to onset and completion of disintegration were significantly faster for the Paracetamol/calcium carbonate containing formulation than for the standard paracetmol formulation (6.4±4.3 versus 46.7±20.5 min, p<0.0001 and 12.9±26.4 versus 69.6±30.2 min, p<0.0001). Similarly, for GE, time to onset (41.9±28.8 versus 85.0±28.2, p<0.0001), $T_{50}$ (72.4±36.4 versus 100.7±30.6, p=0.0013) and $T_{90}$ (128.4±41.2 versus 142±33.8, p=0.10) were shorter for the Paracetamol/calcium carbonate containing formulation than for the standard paracetmol formulation. The time for GE of the standard meal did not differ between the Paracetamol/calcium carbonate containing formulation or the standard paracetmol formulation. Furthermore, while 75% of subjects taking the Paracetamol/calcium carbonate containing formulation showed onset of disintegration/dissolution within 5 mins, none of the standard group exhibited onset at this time point.

Conclusions:

The Paracetamol/calcium carbonate containing formulation had a highly significant in vivo tablet disintegration advantage over the standard paracetamol formulation in this scintigraphy study. This correlates with enhanced GE for paracetamol with the Paracetamol/calcium carbonate containing formulation compared with standard paracetamol formulations.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A method for reducing intrapatient variability in paracetamol containing formulations in patients having gastric dysmotility comprising administering to said patient in need thereof an orally administered pharmaceutical dosage comprising paracetamol present in an amount of about 60 to about 80% by weight as a first active agent, calcium carbonate present in an amount of about 5 to about 20% by weight, at least one first binding agent, and at least one disintegrating agent as intragranular components in the form of a granulate, and as an extragranular component at least one hydrophilic colloid.

2. The method according to claim 1 wherein the patient is a diabetic patient.

3. The method according to claim 1 wherein extragranular agent comprises a second binding agent present in an amount ranging from about 0.1% to about 10.0% by weight of the intragranular binding agent amount therein.

4. The method according to claim 1 wherein the extragranular component comprises a second amount of calcium carbonate present in an amount ranging from about 0.1% to about 10.0% by weight of the intragranular calcium carbonate amount therein.

5. The method according to claim 1 wherein the extragranular component comprises a second active which is paracetamol present in an amount ranging from about 0.1% to about 10.0% by weight of an intragranular first active agent which is paracetamol.

6. The method according to claim 1 wherein the extragranular component comprises a super disintegrant present in an amount ranging from about 0.1% to about 5.0% by weight of the composition.

7. The method according to claim 1 wherein the hydrophilic colloid is selected from alginic acid, carageenan, gellan, pectin, agar or a combination of two or more thereof.

8. The method according to claim 7 wherein the hydrophilic colloid comprises alginic acid.

9. The method according to any of claim 1 wherein the hydrophilic colloid is present in an amount ranging from about 1.0% to about 5.0% by weight of the composition.

10. The method according to any of claim 1 wherein the dosage form further comprises as an extragranular component a colorant, dye, flavorant, sweetener, lubricant, or glidant, or a combination of two or more thereof.

11. The method according to claim 1 wherein the dosage form is a swallow tablet comprising paracetamol, calcium carbonate, pregelatinized starch, and any other optional intragranular components combined together in a granulation process to form a granulate, and then admixed with alginic acid and any other optional extragranular components to form a blend, and then compressed to form a tablet.

12. The method according to claim 1 wherein the dosage form is a swallow tablet comprising a granulate containing as intragranular components paracetamol, calcium carbonate, and at least one binding agent which is microcrystalline cellulose or starch, and wherein the starch is selected from the group consisting of corn starch, modified corn starch, wheat starch, modified wheat starch, potato starch, pregelatinized starch or a combination of two or more starches thereof, with the proviso that if the binding agent comprises a mixture of corn starch and pregelatinized starch then the weight ratio of pregelatinized starch to corn starch is greater than from about 3.0 to 1.0; and optionally a disintegrating agent combined together in a granulation process to form a granulate; and containing as extragranular components a hydrophilic colloid selected from alginic acid, carageenan, gellan, pectin, agar or a combination of two or more thereof; and optionally at least one extragranular excipient which is a second active agent, a second amount of calcium carbonate, a second disintegrating agent, a second binding agent, a colorant, dye, flavorant, sweetener, lubricant, or glidant, or a combination of two or more thereof, and the components are compressed into a tablet.

13. The method according to claim 12 wherein the hydrophilic colloid is alginic acid.

14. The method according to claim 12 wherein the hydrophilic colloid is present in an amount ranging from about 1.0% to about 5.0% by weight of the composition.

15. The method according to claim 12 wherein the granulate comprises a disintegrating agent which is a super disintegrant present in an amount ranging from about 0.5% to about 5.0% by weight of the composition.

16. The method according to claim 12 wherein the intragranular binding agent is a pregelatinized starch.

17. The method according to claim 16 wherein the starch is present in an amount ranging from about 5.0% to about 20.0% by weight of the composition.

18. The method according to claim 12 wherein the binding agent comprises a first binding agent and a second binding agent, and wherein the first binding agent is starch.

19. The method according to claim 18 where in the second binding agent is PVP.

20. The method according to claim 1 wherein the intragranular active agent is paracetamol, and is present in an amount ranging from about 60.0% to about 80.0% by weight of the composition.

21. The method according to claim 1 wherein the intragranular calcium carbonate is present in an amount ranging from about 5.0% to about 20.0% by weight of the composition.

22. The method according to claim 1 wherein the intragranular calcium carbonate content in the granulate does not exceed 20.0% by weight of the composition.

* * * * *